United States Patent [19]

Beppu et al.

[11] 4,275,162
[45] Jun. 23, 1981

[54] PROCESS FOR THE PRODUCTION OF SPHINGOMYELINASE

[75] Inventors: Teruhiko Beppu, No. 5-21, 1-chome, Horinouchi, Suginami-ku, Tokyo; Noboru Ando, Fujisawa, both of Japan

[73] Assignees: Chiyoda Chemical Engineering & Construction Co., Ltd., Yokohama; Teruhiko Beppu, Tokyo, both of Japan

[21] Appl. No.: 126,202

[22] Filed: Mar. 3, 1980

[30] Foreign Application Priority Data

Mar. 9, 1979 [JP] Japan ................................. 54-26794

[51] Int. Cl.$^3$ .............................................. C12N 9/16
[52] U.S. Cl. ..................................... 435/196; 435/19; 435/874
[58] Field of Search ............................... 435/195–198, 435/18, 19

[56] References Cited

PUBLICATIONS

Biochimica et Biophysica Acta, vol. 528, pp. 247–256 (1978).
Journal of Biochemistry, vol. 84, pp. 55–63 (1978), Tokyo.

*Primary Examiner*—Lionel M. Shapiro
*Attorney, Agent, or Firm*—Frishauf, Holtz, Goodman & Woodward

[57] ABSTRACT

A process for the production of sphingomyelinase comprising cultivating a sphingomyelinase-producing microorganism, belonging to the genus Pseudomonas, in a culture medium and recovering sphingomyelinase from the culture medium.

9 Claims, No Drawings

PROCESS FOR THE PRODUCTION OF SPHINGOMYELINASE

BACKGROUND OF THE INVENTION

1. Field of the Invention

This invention relates to a process for the production of sphingomyelinase, and more particularly to a process for producing sphingomyelinase which comprises cultivating a microorganism belonging to the genus Pseudomonas in a culture medium and recovering sphingomyelinase from the culture medium.

2. Description of the Prior Art

Sphingomyelin is one of the phospholipids occurring in high concentrations in a living body. The content of sphingomyelin in blood serum amounts to about 20% of all the phospholipids contained therein, ranking next to that of phosphatidylcholine. It is known that sphingomyelin is decomposed into ceramide and phosphorylcholine by the enzyme sphingomyelinase, and this enzyme is found in animal tissue.

In general, microorganisms do not contain sphingomyelin. Some of phospholipase C produced by microorganisms decompose sphingomyelin, but they also decompose other phospholipids at the same time. Thus, no sphingomyelinase acting selectively on sphingomyelin has been found.

Determinative analysis of phospholipids, such as sphingomyelin by fractionation, is useful for classification of the types of hyperlipemia, and also for diagnosis of arteriosclerosis. Therefore, it has been desired to produce stable sphingomyelinase which enables said determinative analysis by fractionation to be carried out.

SUMMARY OF THE INVENTION

The major object of this invention is to produce sphingomyelinase, which acts selectively on sphingomyelin, by cultivation of microorganisms.

It has now been discovered that a mircoorganism belonging to the genus Pseudomonas, which has been isolated from compost, produces sphingomyelinase.

Therefore, this invention provides a process for producing sphingomyelinase which comprises cultivating a microorganism belonging to the genus Pseudomonas in a culture medium and recovering the formed sphingomyelinase from the culture medium.

DETAILED DESCRIPTION OF THE INVENTION

The microorganism for use in the process of this invention has been isolated from compost and named Pseudomonas sp. T-1. The mutant obtained by irradiating Pseudomonas sp. T-1 with ultraviolet rays is Pseudomonas sp. t-1-43.

The microbial characteristics and properties of Pseudomonas sp. T-1 are as follows:

(1) Morphological Properties
  (a) Form: Short rod-shaped (b) Dimension: 0.5×1.0 micron (the length is changeable to 1 to 5 microns depending on the cultivation conditions)
  (c) Polymorphism: Negative
  (d) Motility: Motile
  (e) Attachment of Flagella: Uni-polar, single
  (f) Sporogenicity: Non-sporulating
  (g) Gram's Stain: Negative
  (h) Acid-fastness: Negative (2) Growth Characteristics in Various Kinds of Culture Media
  (a) Bouillon Agar Plate
    Growth is good: Colony is circular; Elevation is flat; Border is wavy; Surface is smooth and bitter orange; Lustrous; and Viscous.
  (b) Bouillon Agar Slant
    Growth is good; Colony is in the diffused form; and other characteristics are the same as for the bouillon agar plate.
  (c) Bouillon Fluid
    Growth is good; become turbid; and no growth on the surface.
  (d) Bouillon Gelatin Stab Culture
    Liquidation of gelatin takes place.
  (e) Litmus Milk
    No acid is formed; and Coagulation occurs.

(3) Physiological Properties
  (a) Reduction of Nitrates: Negative
  (b) Denitration: Negative
  (c) MR Test: Negative
  (d) VP Test: Negative
  (e) Production of Indole: Negative
  (f) Production of Hydrogen Sulfide: Negative
  (g) Hydrolysis of Starch: Negative
  (h) Utilization of Citric Acid: Positive
  (i) Utilization of Inorganic Nitrogen Sources:
    Ammonia: Positive
    Nitric Acid: Negative
  (j) Production of Pigment: Positive
  (k) Urease: Negative
  (l) Oxidase: Positive
  (m) Catalase: Positive
  (n) Growth Range:
    pH: 5.5 to 10
    Temperature: 10° to 43° C.
  (o) Attitude Toward Oxygen: Aerobic
  (p) O-F Test: Negative
  (g) Fermentation of Saccharides: Negative
  (r) Utilization of β-Hydroxybutyrate: No assimilation
  () Decomposition of Arginine: Positive
  (t) Production of Pigment: Water-soluble, yellow-green, fluorescent pigment is formed in the King B medium.

The above data indicate that the microorganism of this invention belongs to the genus Pseudomonas. According to *Bergey's Manual of Determinative Bacteriology* (8th Ed.), it is included in the Fluorescent, and it is most similar to *Pseudomonas fluorescens* in that it forms a fluorescent pigment and decomposes arginine, the oxidase reaction is positive and the catalase reaction is positive, and in that it hydrolyzes gelatin. However, detailed comparison of these microorganisms reveals that they are clearly different from each other in the following respects:

(1) The microorganism of this invention grows at 41° C.

(2) The O-F Test of the microorganism of this invention is negative.

Therefore, the microorganism of this invention is novel and has been named Pseudomonas sp. T-1. This microorganism has been deposited in the Fermentation Research Institute under the accession number FERM-P-4847 and also in the Institute for Fermentation, Osaka, under the accession number IFO 14009.

This microorganism, as with other microorganisms, can have its characteristics artificially varied by application of, for example, ultraviolet rays, x-rays, radiations, chemicals, etc. The mutant thus obtained can be used in the process of this invention as long as it is a microorganism belonging to the genus Pseudomonas, which possesses the ability to produce sphingomyelinase. For example, the mutant Pseudomonas sp. T-1-43, obtained by irradiating Pseudomonas sp. T-1 with ultraviolet rays, possesses sphingomyelinase-producing ability. It has been deposited in the Fermentation Research Institute under the accession number FERM-P-4848 and also in the Institute for Fermentation, Osaka, under the accession number IFO 14010.

Pseudomonas sp. T-1 requires induction by sphingomyelin, lecithin and the like to produce a substantial amount of the enzyme sphingomyelinase, and the elution of the product enzyme into a culture medium is poor. On the other hand, with Pseudomonas sp. T-1-43, no induction is needed. The sphingomyelinase produced as aforesaid is eluted into the culture medium, and the ability to produce it is improved.

Cultivation of these microorganisms is carried out by conventional procedures in a culture medium as utilized in the cultivation of microorganisms belonging to the genus Pseudomonas. For example, glucose, glycerol, molasses, dextrin and the like can be used as carbon sources; and peptone, meat extract, corn steep liquor, tryptone and the like as nitrogen sources. As indicated, such additional culture medium components as inorganic salts can be added.

Although the above microorganisms grow at a temperature ranging between 10° C. and 43° C., and at a pH ranging between 5.5 and 10, they are usually cultivated at a temperature of 30° to 37° C. and at a pH of 7 to 8, with aeration and stirring. The production of the desired enzyme (sphingomyelinase) reaches a maximum at the stationary phase. Assuming that the amount of enzyme (sphingomyelinase) required for decomposing 1 micromole of a substrate (sphingomyelin) in one minute at 30° C. is one unit, sphingomyelinase is produced in a ratio of about one unit per milliliter of the culture solution.

Confirmation of the formation of sphingomyelinase is carried out as follows: 100 micrograms of sphingomyelin are added to 1 milliliter of the culture solution and reacted at 30° C. for one hour, and a decrease in the amount of sphingomyelin is measured by thin-layer chromatography. When said enzyme is contained in the microbial cells, confirmation thereof can be established by the same procedure using the disrupted cells.

Recovery and purification of sphingomyelinase can be carried out by various procedures. The following efficient procedure exemplifies the foregoing.

A culture broth is subjected to centrifugal separation to obtain a culture solution as a supernatant fluid. The culture solution is then subjected to salting-out by adding ammonium sulfate until 60% saturaton is achieved. Centrifugal separation is again carried out. A precipitate is recovered, and it is then dissolved in 20 millimoles of tris-buffer solution of pH 8. Thereafter, salting-out is conducted by adding ammonium sulfate until 30% saturation is achieved. The precipitate is separated by centrifugal separation and is again dissolved in 20 millimoles of tris-buffer solution of pH 8. The resulting solution is subjected to centrifugal separation to remove impurities, and it is then subjected to dialysis by use of 20 millimoles of tris-buffer solution of pH 8.

Thereafter, the above-obtained enzyme solution is purified by gel-filtration using Sephadex G75 or the like, or by ion-exchange using DEAE cellulose, Cm cellulose or the like. The desired enzyme can be concentrated to 10 units per milliliter.

The enzyme solution obtained by the above procedure had no activity against phosphatidylcholine and phosphatidylethanolamine, and the activity thereof against lysophosphatidylcholine is 1% or less.

The enzyme produced by this invention decomposes sphingomyelin into ceramide and phosphorylcholine. The stable pH range of the enzyme is between 6 and 9 (5° C., 24 hours). More preferably, it is from 7.0 to 8.5. A suitable temperature for the enzyme is from 20° to 50° C., and when allowed to stand at 60° C. for one hour, the enzyme loses its activity (deactivation). It is activated by $Mg^{++}$ ion or detergents such as deoxycholic acid and the like, and it is stabilized by glycerol and the substrate, sphingomyelin. The titer of the enzyme can be measured by the phosphorus calorimetric method using the Fisk-Subbalow reagent.

Sphingomyelinase is, as described above, usable in the fractionation determination of phospholipids and is useful for the classification of the types of hyperlipemia, and is utilized in diagnosis of arteriosclerosis.

The following examples are given to illustrate this invention in detail.

EXAMPLE 1

Pseudomonas sp. T-1 (FERM-P-4847, IFO 14009) was inoculated on a liquid culture medium (pH 7.2) containing 0.8% bouillon, 1% peptone and 0.2% sodium chloride, and it was cultivated with shaking at 30° C. for 12 hours.

The culture broth thus obtained was used as a seed, and 30 milliliters of the seed culture were inoculated into 1.5 liters of a liquid culture medium having the same composition as used above and placed in an Erlenmeyer flask. It was then cultivated with shaking at 30° C. for 6 hours. Thereafter, 100 milligrams of sphingomyelin were added, and the culture broth was cultivated under the same conditions as above for 4 hours.

After cultivation was completed, the culture broth was separated into cells and a culture solution. Tests of the activity of (i) the cells and (ii) the culture solution against sphingomyelin determined that the culture solution had little activity, whereas the cell had activity.

EXAMPLE 2

Pseudomonas sp. T-1-43 (FERM-P-4848, IFO 14010) was inoculated on a bouillon culture medium and cultivated with shaking at 30° C. for 12 hours.

The culture broth thus obtained was used as a seed, and 150 milliliters of the seed culture were inoculated into 15 liters of a liquid culture medium (pH 7.4) containing 2% glycerol, 2% peptone, 1% yeast extract, and 0.5% sodium chloride. It was then cultivated with aeration and stirring in a jar fermentator at 30° C. for 12 hours.

After the cultivation was completed, cells were removed by centrifugal separation and 14 liters of a mother liquor were obtained. It was found by measurement of the mother liquor that the enzyme was produced at a rate of one unit per milliliter of the mother liquor.

The mother liquor was subject to salting-out by adding ammonium sulfate until 60% saturation was achieved. The precipitate thus obtained was dissolved in 20 millimoles of tris-buffer solution (pH 8), and was subject to salting-out by adding ammonium sulfate until 30% saturation was achieved.

The thus-obtained precipitate was dissolved in 20 millimoles of tris-buffer solution (pH 8). The resulting solution was purified by gel filtration using Sephadex G75, and it was further subject to ion-exchange purification using DEAE cellulose. Thus, a purified enzyme solution having a concentration of 10 units per milliliter was obtained.

The thus-obtained enzyme solution had no activity against phosphatidylcholine and phosphatidylethanolamine, and its activity against lysophosphatidylcholine was 0.2% or less.

What is claimed is:

1. A process for producing sphingomyelinase which comprises cultivating a sphingomyelinase-producing microorganism belonging to the genus Pseudomonas in a culture medium to form sphingomyelinase in said culture medium, and recovering said sphingomyelinase from said culture medium.

2. The process of claim 1, wherein said sphingomyelinase-producing microorganism is Pseudomonas sp. T-1 (FERM-P-4847).

3. The process of claim 1, wherein said sphingomyelinase-producing microorganism is Pseudomonas sp. T-1-43 (FERM-P-4848).

4. The proces of claim 1, wherein a culture broth is harvested at the stationary phase.

5. The process of any one of claims 1 through 4, wherein cultivation is carried out a temperature of from 30° to 37° C.

6. The process of any one of claims 1 through 4, wherein cultivation is carried out at a pH of from 7 to 8.

7. The process of claim 5, wherein cultivation is carried out at a pH of from 7 to 8.

8. The process of claim 1 or 2 or 3, wherein cultivation is carried out at a temperature of 10° C. to 43° C.

9. The process of claim 8, wherein cultivation is carried out at a pH of from 5.5 to 10.

* * * * *